US012805887B2

(12) United States Patent
Choe et al.

(10) Patent No.: US 12,805,887 B2
(45) Date of Patent: Nov. 24, 2026

(54) DEVICES AND METHODS FOR TREATING BLOCKED BLOOD VESSELS

(71) Applicant: SHANGHAI WALLABY MEDICAL TECHNOLOGIES CO., INC., Shanghai (CN)

(72) Inventors: Jerome Choe, Los Angeles, CA (US); Earl Bardsley, Marietta, SC (US)

(73) Assignee: Wallaby Medical, LLC, Laguna Hills, IA (US)

( * ) Notice: Subject to any disclaimer, the term of this patent is extended or adjusted under 35 U.S.C. 154(b) by 95 days.

(21) Appl. No.: 18/942,691

(22) Filed: Nov. 9, 2024

(65) Prior Publication Data

US 2025/0160861 A1 May 22, 2025

Related U.S. Application Data

(60) Continuation of application No. 18/511,948, filed on Nov. 16, 2023, now Pat. No. 12,171,446, which is a division of application No. 16/963,898, filed as application No. PCT/US2019/015483 on Jan. 28, 2019, now Pat. No. 11,857,209.

(60) Provisional application No. 62/624,062, filed on Jan. 30, 2018.

(51) Int. Cl.
*A61B 17/22* (2006.01)
*A61B 17/221* (2006.01)

(52) U.S. Cl.
CPC ...... *A61B 17/22012* (2013.01); *A61B 17/221* (2013.01); *A61B 2017/22038* (2013.01); *A61B 2017/22084* (2013.01)

(58) Field of Classification Search
CPC ........ A61B 17/221; A61B 2017/22012; A61B 2017/22038; A61B 2017/22084; A61B 17/22012
USPC .......................................................... 606/128
See application file for complete search history.

(56) References Cited

U.S. PATENT DOCUMENTS

| | | | |
|---|---|---|---|
| 6,511,492 | B1 | 1/2003 | Rosenbluth et al. |
| 6,663,650 | B2 | 12/2003 | Sepetka et al. |
| 6,730,104 | B1 | 5/2004 | Sepetka et al. |
| 6,824,545 | B2 | 11/2004 | Sepetka et al. |
| 7,285,126 | B2 | 10/2007 | Sepetka et al. |
| 7,766,921 | B2 | 8/2010 | Sepetka et al. |
| 8,088,140 | B2 | 1/2012 | Ferrera et al. |
| 8,298,257 | B2 | 10/2012 | Sepetka et al. |
| 8,545,514 | B2 | 10/2013 | Ferrera |
| 8,632,584 | B2 | 1/2014 | Henkes et al. |
| 8,777,976 | B2 | 7/2014 | Brady et al. |
| 8,814,892 | B2 | 8/2014 | Galdonik et al. |

(Continued)

FOREIGN PATENT DOCUMENTS

CN 106108980 A 11/2016

*Primary Examiner* — Kankindi Rwego
(74) *Attorney, Agent, or Firm* — Helen S. Liu

(57) ABSTRACT

The present teachings provide devices and methods of engaging, capturing, and retrieving emboli. Specifically, one aspect of the present teachings provides a device comprising a generally cylindrical body, with its proximal ends joining to a delivery system and a plurality of cells forming its luminal surface. The cylindrical body is configured to axially rotate as it radially expands. Another aspect of the present teachings provides a device comprising two elongated bodies one disposed within the other. As the device expands radially, both elongated bodies are configured to axially rotate independently.

4 Claims, 10 Drawing Sheets

(56) References Cited

U.S. PATENT DOCUMENTS

| | | | |
|---|---|---|---|
| 8,852,205 B2 | 10/2014 | Brady et al. | |
| 8,945,172 B2 | 2/2015 | Ferrera et al. | |
| 9,198,687 B2 | 12/2015 | Fulkerson et al. | |
| 9,220,522 B2 | 12/2015 | Fulkerson et al. | |
| 9,271,820 B2 | 3/2016 | McIntosh et al. | |
| 9,301,769 B2 | 4/2016 | Brady et al. | |
| 9,351,749 B2 | 5/2016 | Brady et al. | |
| 9,402,707 B2 | 8/2016 | Brady et al. | |
| 9,433,429 B2 | 9/2016 | Vale et al. | |
| 9,445,829 B2 | 9/2016 | Brady et al. | |
| 9,463,036 B2 | 10/2016 | Brady et al. | |
| 9,585,741 B2 | 3/2017 | Ma | |
| 9,642,635 B2 | 5/2017 | Vale et al. | |
| 9,642,639 B2 | 5/2017 | Brady et al. | |
| 10,299,811 B2 | 5/2019 | Brady et al. | |
| 10,363,054 B2 | 7/2019 | Vale et al. | |
| 10,390,850 B2 | 8/2019 | Vale et al. | |
| 10,463,386 B2 | 11/2019 | Ogle et al. | |
| 10,588,648 B2 | 3/2020 | Brady et al. | |
| 11,857,209 B2 * | 1/2024 | Choe | A61B 17/22012 |
| 2005/0209678 A1 | 9/2005 | Henkes et al. | |
| 2011/0060359 A1 | 3/2011 | Hannes et al. | |
| 2012/0277788 A1 | 11/2012 | Cattaneo | |
| 2013/0131690 A1 | 5/2013 | Nagl et al. | |
| 2013/0184739 A1 | 7/2013 | Brady et al. | |
| 2014/0277079 A1 * | 9/2014 | Vale | A61B 17/221 606/200 |
| 2014/0379023 A1 | 12/2014 | Brady et al. | |
| 2016/0106448 A1 | 4/2016 | Brady et al. | |
| 2016/0113664 A1 | 4/2016 | Brady et al. | |
| 2016/0242893 A1 | 8/2016 | Joshi et al. | |
| 2016/0256255 A9 | 9/2016 | Ma | |
| 2017/0119408 A1 | 5/2017 | Ma | |
| 2017/0119409 A1 | 5/2017 | Ma | |
| 2018/0325537 A1 | 11/2018 | Shamay et al. | |

* cited by examiner

DEVICES AND METHODS FOR TREATING BLOCKED BLOOD VESSELS

CROSS REFERENCE TO RELATED APPLICATIONS

This application is a Continuation Patent Application of U.S. patent application Ser. No. 18/511,948, filed on Nov. 16, 2023, which is a Division Patent Application of patent application Ser. No. 16/963,898, filed on Jan. 18, 2019, which is a National Stage Entry under 37 U.S.C. § 371 of International Application No. PCT/US19/15483, filed on Jan. 28, 2019, which claims priority to and the benefit of U.S. Provisional Patent Application Ser. No. 62/624,062, entitled "Devices And Methods For Treating Blocked Blood Vessels," filed Jan. 30, 2018. The entirety of each of U.S. application Ser. No. 18/511,948, U.S. application Ser. No. 16/963,898, PCT Patent Application Number PCT/US19/15483, and U.S. Provisional Application Ser. No. 62/624,062 is incorporated herein by reference.

FIELD

The present teachings relate to minimally invasive catheter and methods of minimally invasive catheter delivered embolic capture devices for use in the vasculature, especially those suited for usage in the brain and vessel systems perfusing the same.

BACKGROUND

Mechanical thrombectomy devices seek to salvage ischemic but not yet fully infarcted brain; coronary, peripheral system blood clot in legs; and/or venous site; by restoring perfusion through the initially occluded artery. Each class of mechanical thrombectomy devices achieves recanalization through somewhat different biomechanical mechanisms.

There are three types of catheter thrombectomy devices on the market-aspiration catheters to vacuum the clot out of the vessel, lytic deliver catheters to infuse the clot with targeted thrombotic drug treatment, and mechanical thrombectomy systems that Engage and retract clot. The systems on the market may combine one or more of these attributes. There are pros and cons to each of these approaches.

The aspiration catheters employ vacuum aspiration to remove occlusive clot in acute ischemic stroke. While manual aspiration of target thrombi can be performed through any microcatheter, such as by applying suction through a bore small enough to fit within intracranial arteries. The aspiration catheters are often used in rapid single-session flow restoration for removing small, fresh, soft thrombus. However, larger and more organized thrombus can overwhelm and emboli the small aperture of a manual aspiration catheter. In addition, manual aspiration is more likely than mechanical methods to leave residual thrombus. Additionally, aspiration catheters, generally having a large profile, have difficulty in crossing lesions.

The lytic delivery catheters directed thrombolysis (CDT) is the localized delivery of lytic via a catheter to dissolve thrombus and to restore vascular flow. Although the lytic therapy offers improved outcomes versus the standard anti-coagulation therapy, the lytic therapy alone is often not fast enough to resolve a critical coronary blockage as found in STEMI or in restoring flow in peripheral vasculature. In peripheral cases, a lytic-only treatment may require extended stays in the ICU and frequent angiographic re-visualizations to check the progress. To treat a large thrombus burden of the neuro vasculature, a significant systemic dose of lytic is often used before the blockage can be fully resolved. Such higher doses of lytic delivery could increase the risk of bleeding.

Mechanical thrombectomy, in conjunction with systemic thrombolysis, is currently the standard of care for the treatment of acute ischemic stroke. There are two kinds of mechanical thrombectomy systems, coil retriever and stent retriever. The coil retrievers are composed of Nitinol shape-memory wire and delivered through a microcatheter across the target clot. As the device is extruded from delivery catheter, it immediately reassumes its native coil form. The neurointerventionalist deploys the loops of the coil through the clot to engage the thrombus, and then pulls both coil and clot back into the catheter, like pulling a cork from a wine bottle. The stent retrievers are self-expanding stents that are deployed in the occluded vessel within the thrombus, engaging it and entangling it within the stent struts. The stent and thrombus are then withdrawn back into the delivery catheter.

With the capability of restoring flow in a single session, a stent retriever may remove a higher percentage of clot than the manual aspiration methods and can restore flow in a significantly less time than the lytic treatment alone. Despite their superiority in improving clinical outcomes in patients with acute ischemic strokes, however, stent retrievers are not without complications. Recent studies have found that these devices could cause vascular damage that extends into the medial layer of an artery. Another common disadvantage of stent retriever is that stent retrieval necessarily induces clot fragmentation, which may result in distal embolization and occlusion of previously uninvolved territory. Thus, room for improvement remains.

SUMMARY

One aspect of the present teachings provides an embolic capture device. In various embodiments, the embolic capture device comprising an elongated stent body and at least two connecting struts attaching the elongated stent body to a pusher shaft. The elongated stent body has a distal end, a proximal end, an axial lumen extending from the distal end to the proximal end, and a luminal surface. The luminal surface of the elongated body has a plurality of cells. Each cell has a distal end, a proximal end, and a cell axis extending through both distal and proximal ends. At least one cell has a cell axis forming an acute angle with a longitudinal axis of the elongated body. The embolic capture is configured to have an identical material mass across its entire circumference at any axial location. The embolic capture device has a radially collapsed profile during delivery and a radially expanded profile upon deployment.

In one aspect of the present teachings, each cell forming the luminal surface of the embolic capture device is formed by two struts. At least one cell has different struts profile from at least one other cell. In another aspect of the present teachings, at least one cell is formed by two wavy profiled struts, configured to be symmetrical across a center of the cell axis between the distal and proximal ends of the cell.

In one aspect of the present teachings, all cells forming the luminal surface of the embolic capture device have the cell axis that are parallel to each other. In another aspect of the present teachings, each cell has a height and length, and wherein at least one cell has a different height to length ratio from at least one other cell.

In one aspect of the present teachings, the device is configured to axially rotate in a direction toward the distal end of the cell as said cell expands radially. In one aspect of the present teachings, the device is configured to axially rotate in a clock wise rotation. In another aspect of the present teachings, the device is configured to axially rotate in a counter clock wise rotation. In yet another aspect of the present teachings, the device is configured to axially rotate in a first direction followed by an axial rotation in an opposite direction as it expands radially. In yet another aspect of the present teachings, the device is configured to axially rotate in a first rotation speed followed by an axial rotation in a second rotation speed as it expands radially. In yet another aspect of the present teachings, the device is configured to axially rotate with a first torque strength followed by an axial rotation with a second torque strength as it expands radially.

Another aspect of the present teachings provides an embolic capture device having an inner stent body and at least two connecting struts attaching the inner stent body to a distal end of a pusher shaft; as well as an outer stent body and at least two connecting struts attaching the outer stent body to a distal portion of the pusher shaft proximal to the distal end of the pusher shaft. The outer stent body has a distal end, a proximal end, an axial lumen extending from the distal end to the proximal end, and a luminal surface. An inner stent body has a distal end, a proximal end, an axial lumen extending from the distal end to the proximal end, and a luminal surface. The inner stent body is disposed within the axial lumen of the outer stent body. The distal end of the inner stent body extends beyond the distal end of the outer stent body. The device has a radially collapsed profile during delivery and a radially expanded profile upon deployment.

In one aspect of the present teachings, the luminal surfaces of the inner stent body has a plurality of cells. Each cell has a distal end, a proximal end, and a cell axis extending through both distal and proximal ends. And at least one cell axis forms an acute angle with a longitudinal axis of the elongated body.

In another aspect of the present teachings, the luminal surfaces of the outer stent body has a plurality of cells. Each cell has a distal end, a proximal end, and a cell axis extending through both distal and proximal ends. And at least one cell axis forms an acute angle with a longitudinal axis of the elongated body.

In one aspect of the present teachings, at least one of the inner and outer stent body is configure to axially rotate as the device deploys into the radially expanded profile. In another aspect of the present teachings, the inner stent body is configured to axially rotate in a first direction, and the outer stent body is configured to axially rotate in an opposite direction. In yet another aspect of the present teachings, the inner stent body is configured to axially rotate in a first rotation speed, and the outer stent body is configured to axially rotate in a second rotation speed. In yet another aspect of the present teachings, the inner stent body is configured to axially rotate with a first torque strength, and the outer stent body is configured to axially rotate with a second torque strength. In yet another aspect of the present teachings, at least one of the inner and outer stent body is configure to axially rotate in a first direction followed by an axial rotation in an opposite direction as it expands radially. In yet another aspect of the present teachings, at least one of the inner and outer stent body is configure to axially rotate in a first rotation speed followed by an axial rotation in a second rotation speed as it expands radially.

In one aspect of the present teachings, the distal ends of the inner stent body is disposed distal to the distal end of the outer stent body.

DETAILED DESCRIPTION

Figure 1:
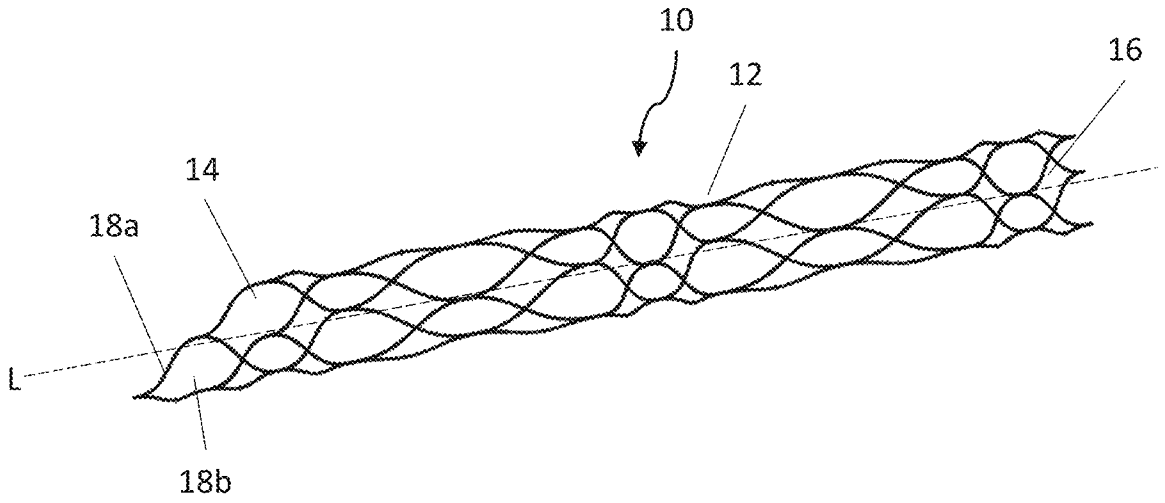
FIG. 1 is a perspective view of an exemplary device in accordance with the present teachings.

In one aspect, the present teachings are described more fully hereinafter with reference to the accompanying drawings, which show certain embodiments of the present teachings. The present teachings may, however, be embodied in many different forms and should not be construed as limited to the embodiments set forth herein; rather, these embodiments are provided to illustrate various aspects of the present teachings. Like numbers refer to like elements throughout.

In one aspect, the present teachings provide catheter-based emboli removal systems. In some embodiments, a system of the present teachings is used to remove blood clots from vessels in the body. In some embodiments, the vessels are veins and/or artery. In some embodiments, the system is used to treat, in veins, deep vein thrombosis (DVT), and in arteries, pulmonary embolism (PE), ST-elevated myocardial infarction (STEMI) and ischemic stroke. In some embodiments, the systems can also quickly clear dialysis arteriovenous grafts, which are prone to thrombus formation. According to some embodiments, when the catheter-based emboli removal system of the present teachings is deployed into a blood vessel, the emboli removal device is expanded and moved proximally along the vessel so that the embolus is substantially contained with a mesh basket of the emboli removal device. Specifically, the present teachings provide a device/system and methods of removing neurocranial emboli without causing any distal complication arising from the dislodgement of larger pieces of a recovered embolus distal to the location of the original embolus.

As used herein, the terms “radially outward” and “radially away” means any direction which is not parallel with the central axis. For example, considering a cylinder, a radial outward member could be a piece of wire or a loop of wire that is attached or otherwise operatively coupled to the cylinder that is oriented at an angle greater than 0° relative to the central longitudinal axis of the cylinder.

As used herein, the term “lumen” means a canal, duct, generally tubular space or cavity in the body of a subject, including veins, arteries, blood vessels, capillaries, intestines, and the like. The term “lumen” can also refer to a tubular space in a catheter, a microcatheter, or the like in a device.

As used herein the term “proximal” shall mean closest to the operator (less into the body) and “distal” shall mean furthest from the operator (further into the body). In positioning the medical device from a downstream access point, distal is more upstream and proximal is more downstream.

As used herein the term “emboli” used herein can be clot, thrombus or the like, and these terms may be used interchangeably.

As explained in further detail below, various embodiments of the present teachings provide medical devices/system for removing blood clots from a vessel in the body. In some embodiments, the medical devices/system according to the present teachings may include an embolic capture device or means configured to capture the clot. In some embodiments, a pusher shaft joins the embolic capture device. In some embodiments, the pusher shaft pushes and/or pulls, the embolic capture device. In some embodiments, the embolic capture device according to the present teachings may be extended into an elongated profile for percutaneous delivery, and resume to a radially expanded deployment profile for capturing the clot, and be extended into a second elongated profile to retrieve the clot. As used in this application, unless otherwise indicated, the term “vessel” refers to a blood vessel, including an artery, an arteriole, a capillary, a venule, a vein or a network of any of the combinations of the foregoing.

In another aspect, the present teachings disclose an embolic capture device for intracranial use. According to some embodiments, the embolic capture device has a general profile of a stent that is flexible and atraumatic, and is available in various lengths and diameters, thin-walled, and/or radiopaque. In some embodiments, the stent is configured to be precisely delivered, retrieved, and repositioned. In some embodiments, the stent is flexible enough to be delivered via a microcatheter and to be placed in a small vessel but has sufficient radial forces to conform to the vessel wall geometry when deployed.

In another aspect, the present teachings disclose an embolic capture device with an elongated delivery profile. In some embodiments, the embolic capture device has an expanded deployed profile. As described in detail below, in some embodiments, the embolic capture device could have a straightened, elongated, low-profile delivery configuration suitable for delivery via a delivery system. In some embodiments, the deployed configuration of the embolic capture device substantially engages the blood vessel within which it is deployed. When an embolic capture of the present teachings is used to retrieve an emboli, a positioning guide wire is first threaded through the blood vessel across a blood clot. A microcatheter then threads over the positioning guide wire and having its distal end positioned distal to the clot. The positioning guide wire is then removed, followed by a pusher shaft joining to a proximal end of an elongated embolic capture device extending through the lumen of microcatheter. While holding elongated embolic capture device steady, a clinician withdraws the microcatheter proximally to uncover the device. Once outside of the microcatheter, the embolic capture device expands to engage the clot. In one embodiment, the device is deployed distal to the clot. In another embodiment, the device is deployed across the clot. In some embodiments, to retrieve the clot, the clinician pulls the pusher shaft proximally, the embolic capture device is pulled proximally back, carrying the blood clot back into a larger catheter, guide catheter, or distal access catheter (DAC).

The techniques disclosed for delivering and deploying the embodiments described herein are only examples. It should be understood that other techniques can be used instead of, or in combination with, these teachings. For example, the techniques used to deploy an embodiment of the devices described herein depend on the particular features of the device, the delivery system, and the anatomy in which the device is being deployed.

FIG. 1 shows an exemplary embolic capture device (10) for insertion into a human vasculature according to the present teachings. The device (10) can be used, for example, to remove blood clots. This present teachings can also be applied to other medical devices, for example, stents, flow dividers, filters, and the like. The device is particularly suitable in stent-like systems that are used to influence flow. This present teachings can be generally applied to implants or other medical devices that can be released temporarily in the body and be retractable into the corresponding delivery system. The retractability can play a role in repositioning a device, such as stents, or generally in the recovery of a temporarily released medical device.

Figure 2A:
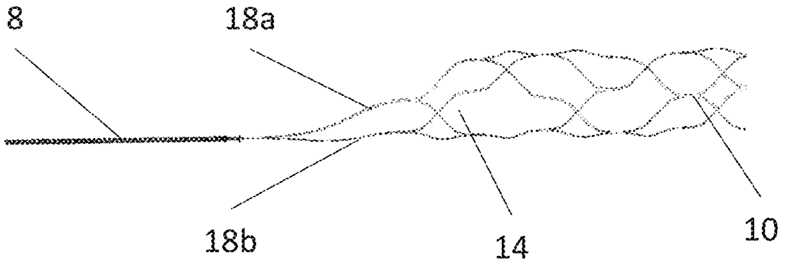
FIGS. 2A-2B are perspective views of various exemplary attachment mechanism between a proximal end of the exemplary device and a distal end of a pusher shaft in accordance with the present teachings.
Figure 2B:
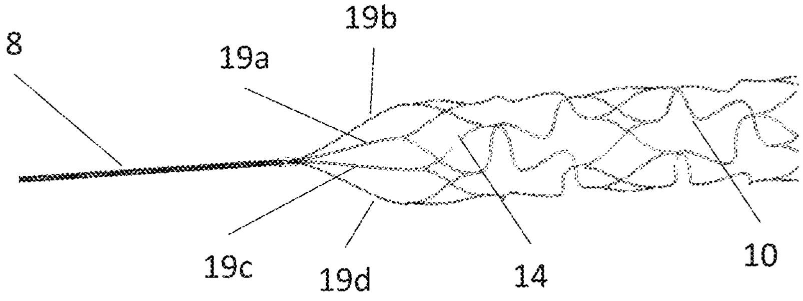

FIG. 1 shows an embodiment of the embolic capture device (10) of the present teachings in its pre-set deployed configuration. The embolic capture device (10) comprises a hollow stent body (12) with a generally cylindrical shape, a proximal end (14) and a distal end (16). The stent body (12) of the embolic capture device (10) also has a longitudinal axis “L”. The proximal end (14) of the stent body (12) joins to a distal end of the pusher shaft (not shown) of a delivery system (not shown) by a plurality of struts (18*a*, 18*b*). For example, two connecting struts (18*a*, 18*b*) at the proximal end of the stent body (12) are joined together with a distal end of the pusher shaft (8) by a marker band forming an off centered attachment between the proximal end (14) of the device (10) and the distal end (16) of the pusher shaft (8), for example, such as one shown in FIG. 2A. In another embodiment, four connecting struts (19*a*, 19*b*, 19*c*, 19*d*) at the proximal end of the stent body (12) are attached together with a distal end of the pusher shaft (8) forming a balanced, more symmetrical attachment between the proximal end (14) of the embolic capture device (10) and the pusher shaft (8), for example, such as shown in FIG. 2B. In one embodiment, the pusher shaft (8) is fixedly attached to the device (10). In an alternative embodiment, attachment between the pusher shaft (8) and the device (10) is detachable.

Figure 2C:
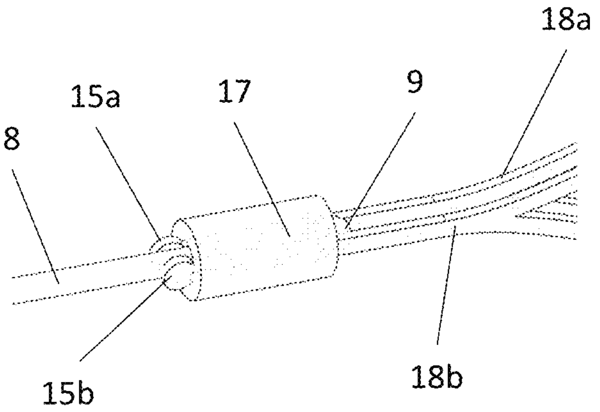
FIG. 2C is a perspective detailed view of an exemplary attachment between the proximal end of the exemplary device and a distal end of a pusher shaft in accordance with the present teachings.

FIG. 2C illustrates a detailed view of the connection between the stent body (12) and pusher shaft (8). As shown in the figure, a marker band (17) in a shape of a tube is attached over the proximal ends of two connecting struts (18*a*, 18*b*) and the distal end of the pusher shaft (8). According to one embodiment, the proximal ends (15*a*, 15*b*) of the connecting struts (18*a*, 18*b*) are formed into a flat disk shape, the distal end (9) of the pusher shaft (8) is formed into an enlarged profile that is greater than the inner diameter of the marker band (17). As seen in the figure, the proximal disc ends (15*a*, 15*b*) connecting struts (18*a*, 18*b*) extends beyond the proximal end of the marker band tube (17), the distal ball end (9) of the pusher shaft (8) extends beyond the distal end of the marker band tube (17), and as marker band (17) fixed over the connecting struts (18*a*, 18*b*) and the distal end (9) of the pusher shaft (8), a mechanical lock is formed between the pusher shaft (8) and the stent body (12). According to one embodiment, such mechanical lock is configured to create a tensile force between the pusher shaft and the embolic capture device of 5N to 15 N. Additionally, in some embodiments, the mechanical lock between marker band and the pusher shaft as well as the pusher shaft could be formed by crimping, adhesive, or both. For example, epoxy or solder could be added to both ends of a crimp lock between the connecting struts and the distal end of the pusher shaft. According to some embodiments, the marker band (1) could be made of material such as platinum tungsten alloy, platinum iridium alloy, or platinum. The marker band (17) could have an overall inner diameter of 0.005" to 0.015", a wall thickness of 0.001" to 0.0025", and a general length between 0.010" to 0.040".

Referring back to FIG. 1, the embolic capture device (10) has a wall in the form of an array of openings, or cells. Each of such cells (20) is configured to expand and collapse laterally. According to one embodiment of the present teachings, the embolic capture device (10) expands upon deployment in vivo. In one embodiment of the present teachings, upon deployment, the embolic capture device (10) expands radially due to the elastic nature of the material. In another embodiment, such radial expansion is achieved by the pre-set thermal shape memory of the device material. In yet another embodiment, such radial expansion is achieved manually via an inflating balloon. In some embodiments, the embolic capture device is made of stainless steel, nitinol, Titanium, Elgiloy, Vitalium, Mobilium, Ticonium, Platinore, Stellite, Tantalum, Platium, Hastelloy, CoCrNi alloys (e.g., trade name Phynox), MP35N, or CoCrMo alloys, any other metallic alloys, or a mixture thereof.

Figure 3:
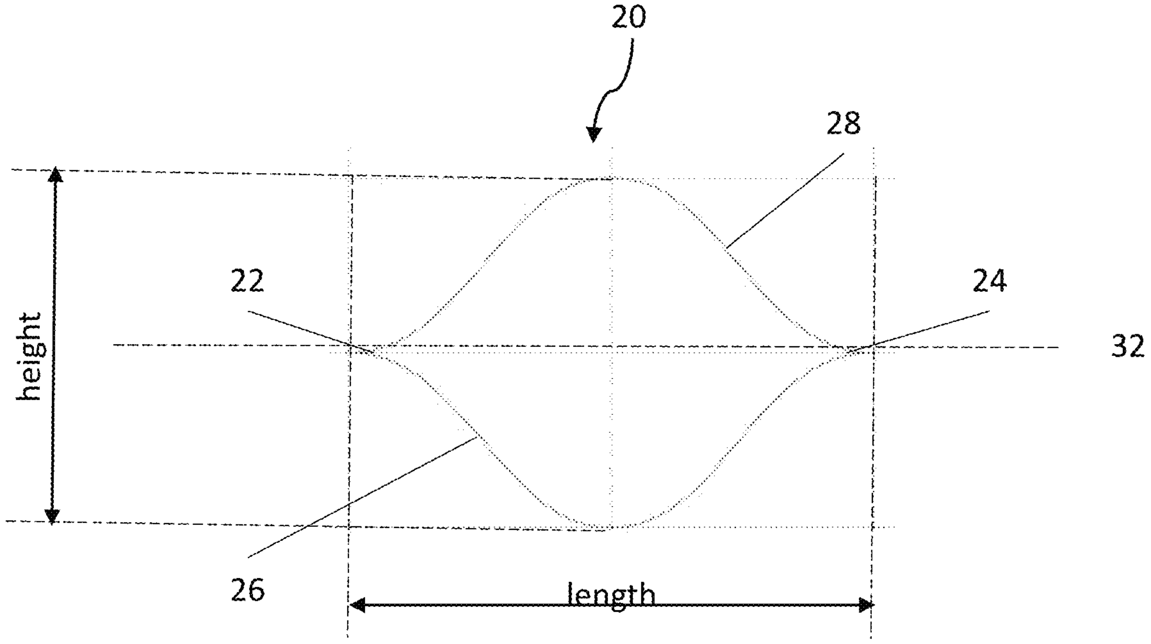
FIG. 3 is a perspective view of cell structure design along the elongated body of the exemplary medical device of FIG. 1 in accordance with the present teachings.

According to some embodiments of the present teachings, the embolic capture device (10) has an array of closed cell structure which allows the device (10) to collapse during the delivery and expands upon the deployment. FIG. 3 illustrates one embodiment of the cell (20) structure design. As illustrated, each cell (20) comprises two continuous struts (26, 28) connected at two spots forming a distal end (24) and a proximal end (22) of the cell (20). As shown, both the struts (26, 28) are pre-formed into an arc with a desired curvature. When the cell (20) is at a relaxed state, two struts (26, 28) arc away from each other as shown in FIG. 3. When the cell (20) collapses, the distal and proximal ends (22) of each cell (20) move away from each other leading to both struts (26, 28) being straighten and moving closer to each other. In one embodiment, the cell (2) has two identical upper and lower ac length and curvature, and a horizontal cell axis.

Figure 4A:
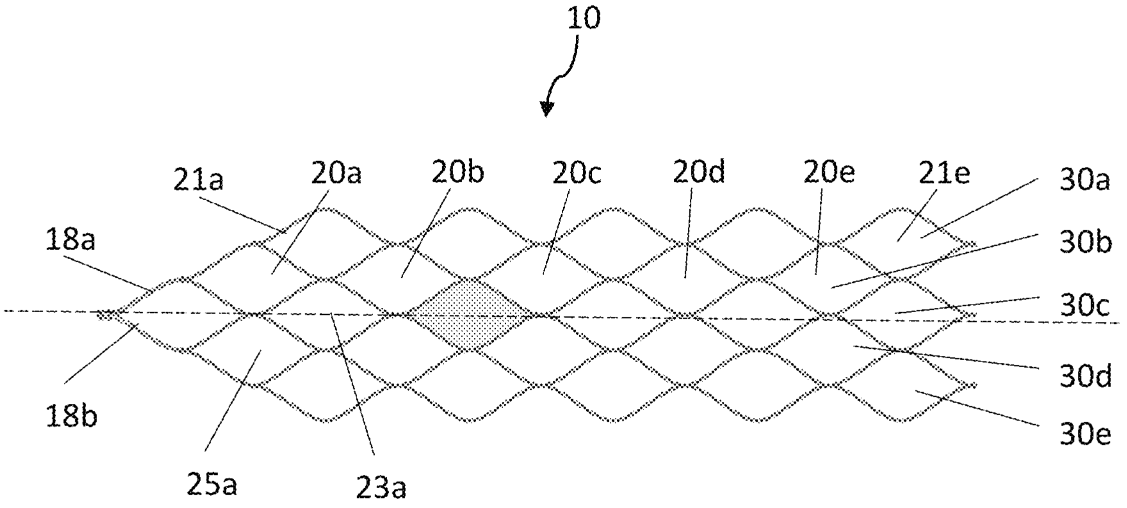
FIGS. 4A-4B are perspective views of various exemplary device in a form of exemplary cell array and struts joining to the proximal end of the device in accordance with the present teachings.

Now referring to FIG. 4A, an embodiment of the embolic capture device (10) is illustrated in an unwrapped configuration. As shown in FIG. 4A, a number of cells (20*a*, 20*b*, 20*c*, 20*d*) connect to each other in a longitudinally direction forming a row of cells (30*b*). In one embodiment, five rows (30*a*, 30*b*, 30*c*, 30*d*, &30*c*) of cells with the same cell number are arranged next to each other in an offset radial fashion. That is the most proximal cell (20*a*) in a row (30*b*) is arranged proximal to the most proximal cell (21*a*) of at least one of its adjacent rows (30*a*), and in turn, the most distal cell (20*e*) in this row (30*b*) is also arranged proximal to the most distal cell (21*e*) of at least one of its adjacent rows (30*a*) as shown in FIG. 4A. The offset distance as shown in FIG. 4A is half of the expanded cell length. That is the proximal end of the cell (21*a*) in row (30*a*) starts at the peak curvature of cell (20*a*) in row (30*b*), and the distal end of the cell (20*e*) in row (30*b*) ends at the peak curvature of cell (21*e*) in row (30*a*). Thus, each cell shares some portions of the struts with adjacent cells. For example, as shown in FIG. 4A, cell (20*a*) share half of the strut with the cell (21*a*), and half of the other strut with cell (23*a*). One skilled in the art should understand that FIG. 4A illustrates an unwrapped version of the stent body. Once forming in a tubular configuration, a $6^{th}$ row of cell would be formed when joining the peak curvature of cells in row 30*a* with the peak curvature of cells in row 30*c*. This $6^{th}$ row of cell would have one less cell number comparing to the adjacent rows (30*a*, 30*c*) of cells. In another embodiment, two struts forming each cells have identical length and symmetrical profile across the horizontal cell axis of each cell, for example as shown in FIG. 4A. In one embodiment, all cells in an embolic capture device have the same shape, size and configuration. In another embodiment, cells in an embolic capture device have various shape, size and configuration.

FIG. 4A further shows that two connecting struts (18*a*, 18*b*), with each of their distal end connecting to the proximal end of one most proximal cells (20*a*, 25*a*), and their proximal ends joining together and attaching to a distal end of the pusher shaft (not shown). According to one embodiment of the present teaching, where rows of the cells making up one device such as the one shown in FIG. 1. According to one embodiment of the present teaching, the device has a longitudinal axis "L" that is parallel to the horizontal cell axis of each row of cells. As shown in FIG. 1, in such exemplary embodiment, the device (10) has a longitudinal lumen with all cell expanded to their pre-set configuration. The closed cell structure forms a complete cylindrical surface along middle and distal portions of the device (10) as shown in FIG. 1. The proximal portion of the device (10) has a partial cylindrical surface formed by rows (30*b*) and (30*d*) of the cells according to one embodiment of the present teaching.

Figure 4B:
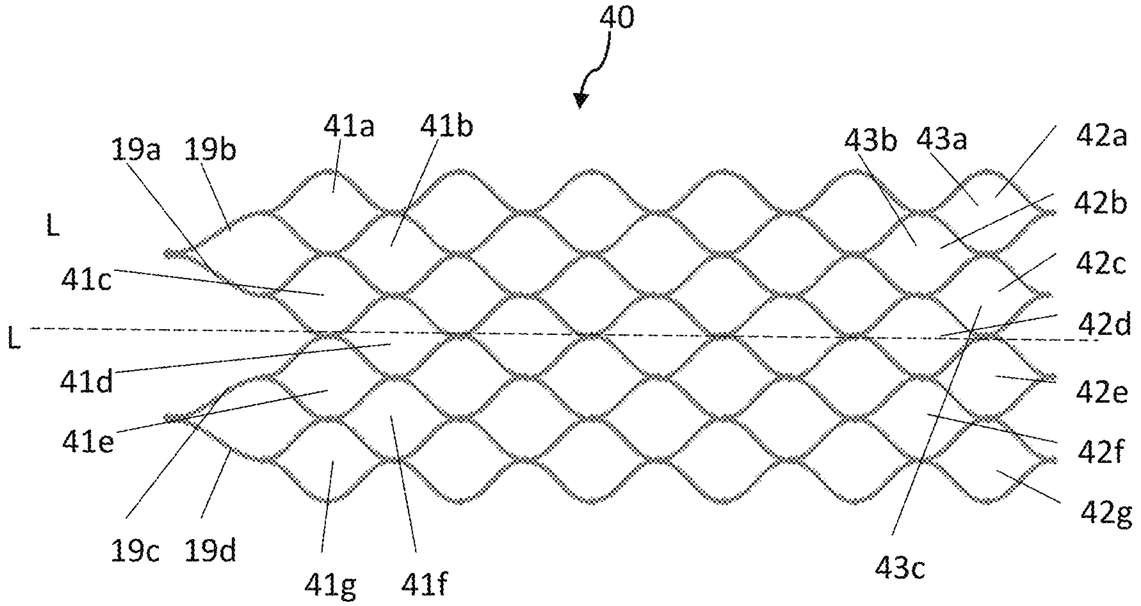

FIG. 4B illustrates another embodiment of present teaching, where the device (40) having four struts (19*a*, 19*b*, 19*c*, 19*d*) connecting to its proximal end in an unwrapped configuration. In this embodiment, the device (40) is made of eight rows of cells arranged in the similar fashion as described above with reference to FIG. 4A. The unwrapped configuration as shown here illustrates 7 rows of cell, one skilled in the art should understand that once forming in a tubular configuration, a $8^{th}$ row of cell would be formed when joining the peak curvature of cells in row 42*a* with the peak curvature of cells in row 42*g*. Unlike exemplary embodiment shown in FIG. 4A, each adjacent rows of cell has different numbers of cells. For example, as shown in FIG. 4B, row 42*b* has 5 cells, and its adjacent rows 42*a* and 42*c*, each has 6 cells. The very proximal cell on row 42*b* starts distal to the very proximal cell on row 42*a* and row 42*c* by a half of the cell strut length. That is, the proximal end of the cell (41*b*) in row (42*b*) starts at the peak curvature of cell (41*a*) in row (42*a*) and at the peak curvature of cell (41*c*) in row (42*c*). Since row 42*b* only has 5 cells, the distal end of the cell (43*b*) in row (42*b*) ends at the peak curvature of cell (43*a*) in row (42*a*), and at the peak curvature of cell (43*c*) in row (42*c*). In another embodiment, two struts forming each cells have identical length and symmetrical curvature across the horizontal cell axis of each cell, for example as shown in FIG. 4A. In one embodiment, all cells forming an embolic capture device have the same shape, size and configuration. In another embodiment, cells in an embolic capture device have various shape, size and configuration.

FIG. 4B further shows that four struts (19*a*, 19*b*, 19*c*, 19*d*), with each of their distal end connecting to the proximal end of the most proximal cells (41*a*, 41*c*, 41*e*, 41*g*), and their proximal ends joining together and attaching to a distal end of the pusher shaft (not shown). According to one embodiment of the present teaching, the device has a longitudinal axis "L" that is parallel to the horizontal cell axis of each row of cells. As shown in FIG. 1, in such exemplary embodiment, the device (40) has a longitudinal lumen with all cell expanded to their pre-set configuration. The closed cell structure forms a complete cylindrical surface along its proximal, middle and distal portions of the device (40).

According to some embodiments, device with four connecting struts at its proximal end general has even number of rows of cells. And device with two connecting struts are its proximal end could have either even or odd number of rows of cells. In another embodiment, for ease the describing various embodiment, illustration are general referring to device with four connecting struts. One skilled in the art should understand that two connecting struts could be incorporated instead of four. In addition, although a certain number of rows and a certain number of cells in one row are illustrated in the exemplary embodiment for the purpose of describing, one skilled in the art should understand, the number of rows, and the number of cells in one row could increase or decrease in order to achieve the treatment purpose.

Continue referring back to FIG. 3, an imaginary line connecting the distal end and the proximal end of each cell forms a cell axis (32). The cell also defines a height and a width as shown in the FIG. 3. The cell length is the linear distance between the distal and proximal ends (22, 24) of the cell (20) in a direction parallel to the longitudinal axis "L". The cell height is the linear distance between the peaks of the cell/cell struts in a direction perpendicular to the longitudinal axis "L". In one embodiment, such as shown in FIG. 3, both struts (26, 28) have the same length and symmetrical arcs across the cell axis (32). In one embodiment, the cell axis (32) is parallel to the longitudinal axis "L" of the device (10) as shown in FIG. 4A. With such configuration, when the device (10) is released from the delivery sheath, the struts (26, 28) forming each cell resume their arc profiles, with their distal and proximal ends (22, 24) moving away from each other, and two struts (26, 28) arc away from each other leading to an expansion of the cell (20) until it reaches its designed height and length. Since the cell axis (32) is parallel to the longitudinal axis "L" of the device (10), and struts forming each cell has the identical length and symmetrical curvature across the cell axis, each cell will expand in a direction perpendicular to the longitudinal axis "L". Thus the device (10) would expand evenly in a radial direction, perpendicular to and radially outward from the longitudinal axis "L" of the device, with no axial rotation around the longitudinal axis.

Figure 5A:
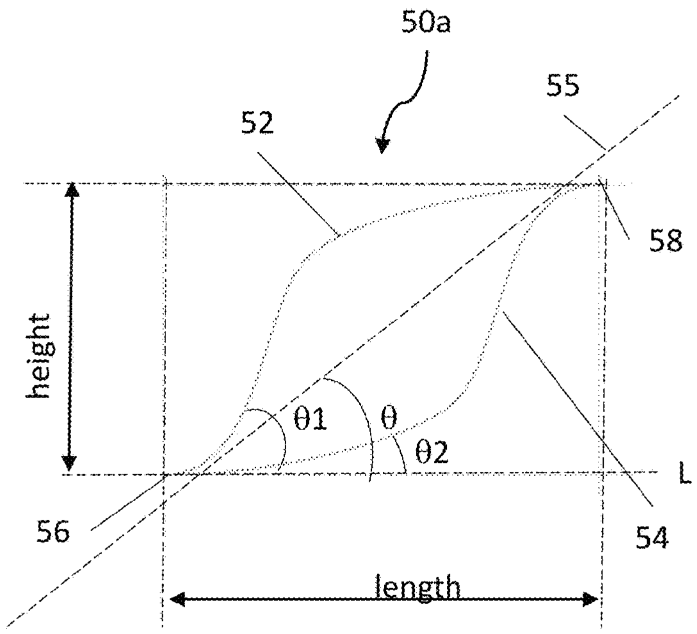
FIGS. 5A-5B are perspective views of various exemplary cell structure design in accordance with the present teachings.

FIG. 5A illustrates another exemplary cell (50) design. In this example, both the struts (52, 54) forming the cell still have the same length. The curvature on each struts (52, 54) are no longer symmetrical across the cell axis. Specifically, the curvature of each struts (52, 54) are rotational symmetrical to each other across the center of the cell (50). Unlike what is shown in FIG. 3, the cell axis (55) angles from the longitudinal axis "L" of the device by "0", as shown in FIG. 5A. With this configuration, when the device is released from the delivery sheath, the distal and proximal ends (56, 58) of the cell (50) move radially away from each other, and the struts (52, 54) forming each cell (50) resume their arc profiles and also arch away from each other leading to an expansion of the cell (50) until it reaches the designed length and height. Since the cell axis (55) angles from the longitudinal axis "L", the direction of both struts (52, 54) expands is no longer perpendicular to the longitudinal axis "L" of the device (50). Thus, instead of expanding in a perpendicular direction to longitudinal axis "L", one strut (52) of the cell expands in an angle "$\theta_1$" to longitudinal axis "L", the other strut (54) of the cell expands in an angle "$\theta_2$" to longitudinal axis "L". With all the cells forming the circumference of the device (60) lumen expand in the above described direction around the longitudinal axis "L", the device would rotate around the axis "L" as it expands.

Figure 5B:
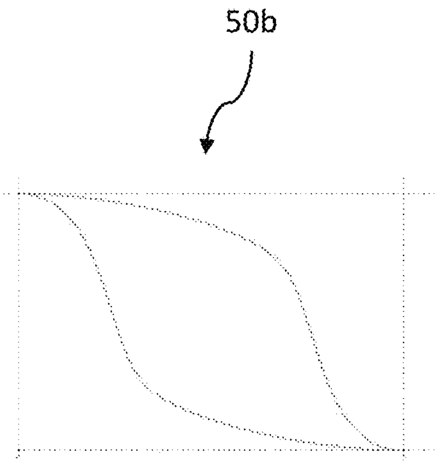

FIG. 5A illustrates the exemplary cell design, where, comparing to the proximal end (56) of the cell (50*a*), the distal end (58) of said cell (50*a*) is clock-wise rotating around the longitudinal axis "L" of the stent body to a degree. In another word, the cell axis, a straight line connecting the proximal end and distal end (56, 58) of the same cell (50*a*) is no longer parallel to the longitudinal axis "L" of the stent body. Thus, during deployment, as the two struts (52, 54) forming the cell (50*a*) arch away from each other, said cell (50*a*) would expand and rotate in a clockwise fashion. Additionally, FIG. 5B illustrates another exemplary cell design, where, comparing to the proximal end of the cell (50*b*), the distal end of said cell (50*b*) is counter clock-wise rotating around the longitudinal axis "L" of the stent body to a degree. In another word, the cell axis, a straight line connecting the proximal end and distal end of the same cell (50*b*) is no longer parallel to the longitudinal axis "L" of the stent body. Thus, during deployment, as the two struts forming the cell (50*b*) arch away from each other, said cell (50*b*) would expand and rotate in a counter clockwise fashion.

According to some embodiments of the present teachings, when the cell height and cell length of each cell are the same so that the angle between the cell axis and the longitudinal axis "L" is about 45°. According to some embodiments of the present teachings, the height and length of each cell are different, such as shown in FIG. 5A. One skilled in the art should understand that the configuration of both cell height and cell length of each cell would result various expansion motion of that cell. In another word, varying cell height and cell length ration could result in different the degree of cell rotation during deployment, and/or the speed of cell rotation during deployment. And a combination of the motion of all cells made up a stent body would in turn affect the overall deployment movement of the stent body. For example, with a greater cell height to cell length ration, said cell would rotates more during expansion. And thus a stent body with cells that having a greater cell height to cell length ratio would rotate more radially during deployment than a stent body with cells that having a less cell height to cell length ratio. In another example, as the cell height to cell length ratio increases, that is as the angle between the cell axis and the longitudinal axis "L" of the device increases, the speed of the axial rotation also increases at a given stent body length.

According to some embodiments of the present teaching, the stent body would be made of cells of same size throughout. In another embodiment, the stent body would be made of cells of various size. In yet another example, a stent body formed with relatively small cells will increase the stiffness and torque strength of the stent body during its axial rotation.

Figure 7:
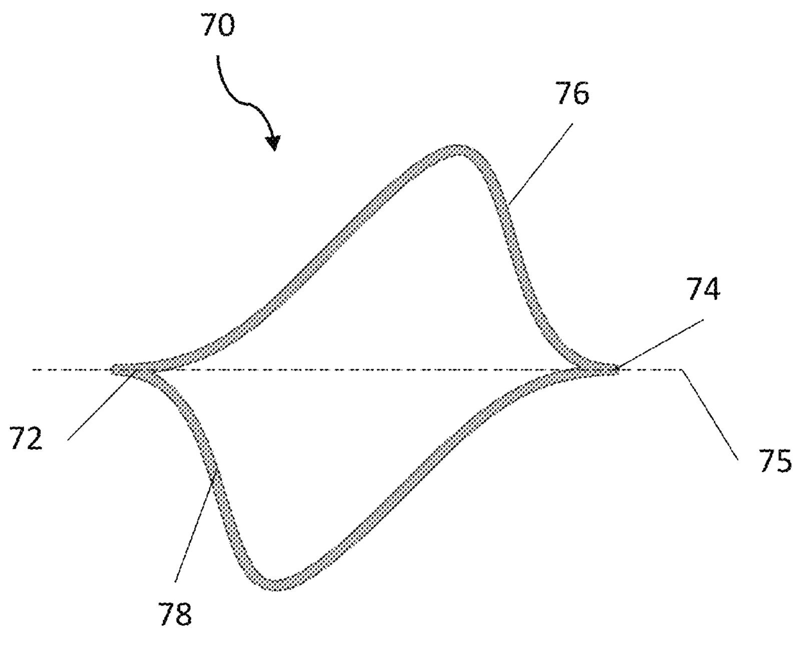
FIG. 7 is a perspective view of cell structure design in accordance with the present teachings.

According to some embodiments of the present teachings, the curvature on both struts (26, 28) are symmetrical across the cell axis (32) as shown in FIG. 3. According to some embodiments of the present teachings, the curvature on one or both the struts could by off-centered, such as shown in FIG. 7. According to another embodiments, the curvature on both struts forming the same cell are not symmetrical across the cell axis, but are rotational symmetrical across the center of the cell axis, such as shown in FIGS. 5A-5B & 7.

Figure 6:
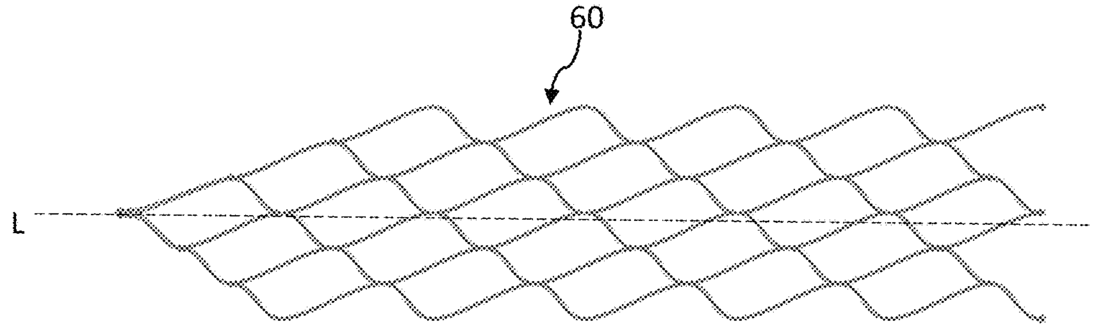
FIG. 6 is a perspective view of an exemplary device in a form of exemplary cell array in accordance with the present teachings.

FIG. 6 illustrates an exemplary embodiment of the stent body where an array of identical cells forms a device (60). As shown in this figure, all cells have identical shape, size and orientation, i.e. all cells have the same cell heights, same cell lengths, and same angle between cell axis and the longitudinal axis "L" of the stent body. As a result, upon a deployment, the device will expand radially while rotate at a steady speed.

One skilled in the art should understand that with a combination of different cell configuration, the stent body could be programmed to have different deployment motion. For example a portion of the stent body could have a clockwise rotation motion, while another portion of the stent body could have a counter clock wise rotation motion. In another example, a portion of the stent body could have accelerated or decelerated rotation speed then the rest portion of the stent body. In yet another example, a portion of the stent body could have a greater rotation range/degree than the rest portion of the stent body.

Figure 8:
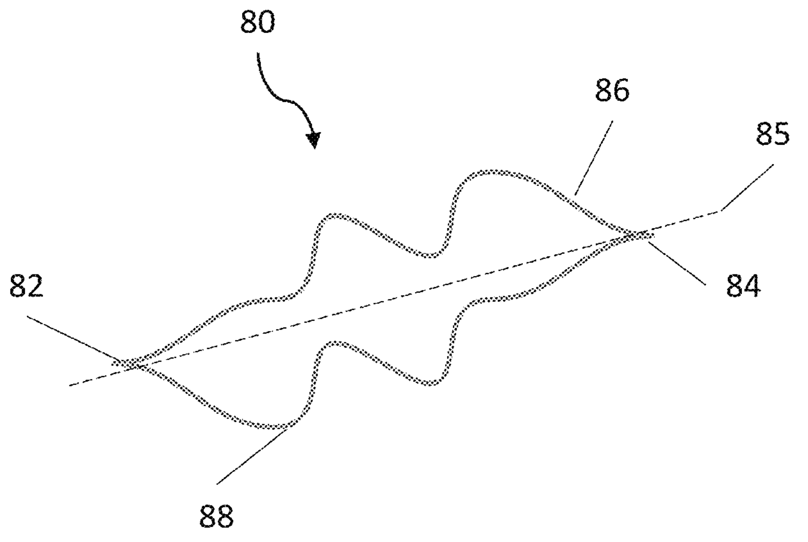
FIG. 8 is a perspective view of cell structure design in accordance with the present teachings.

According to some embodiment, the struts forming the cell could have simple curvature as shown in FIGS. 3, 5 &7. In another embodiment, the struts (86, 88) forming the cell (80) could have a wavy profile, as shown in FIG. 8. Such wavy profile could ensure the stent body to be flexible when deployed at treatment location, and not kink (or collapse) while going through an acute angle, such as tortuous neurovascular paths. As mentioned above, the struts forming the same cell does not have curvature symmetrical across the cell axis. Instead the strut curvature are rotational symmetrical across the center of the cell axis.

In addition to a cell's geometrical construct, the physical character of the struts forming each cell could also affect the performance of the stent body. Specifically, the size of struts forming each cell could directly affect the torque of torsion during cell deployment. According to some embodiments of the present teachings, the size of the struts, i.e. the thickness and the width, forming the same cell could various from cell to cell. As the size of the struts increase, i.e. the width and/or the thickness of the struts increases, the cross section of the struts increases, the torque strength of the device also increases during said cell's deployment rotation. One skilled in the art should understand that a greater rotation torque could lead to a better engagement with blood clot.

Now referring back to FIG. 1, an array of identical cells forms the device (10). Since all the cells have their cell axis parallel to the longitudinal axis "L" of the stent body, upon a deployment, the entire portion of the stent body will expand radially as it exists the microcatheter without any radial twisting. Now referring back to FIG. 6, an array of identical cells forms a device (60). All cells have their cell axis forming a same angle against the longitudinal axis "L" of the stent body, upon a deployment, the stent body will expand radially while rotate radially around the longitudinal axis "L" of the stent body at a steady speed.

Figure 9:
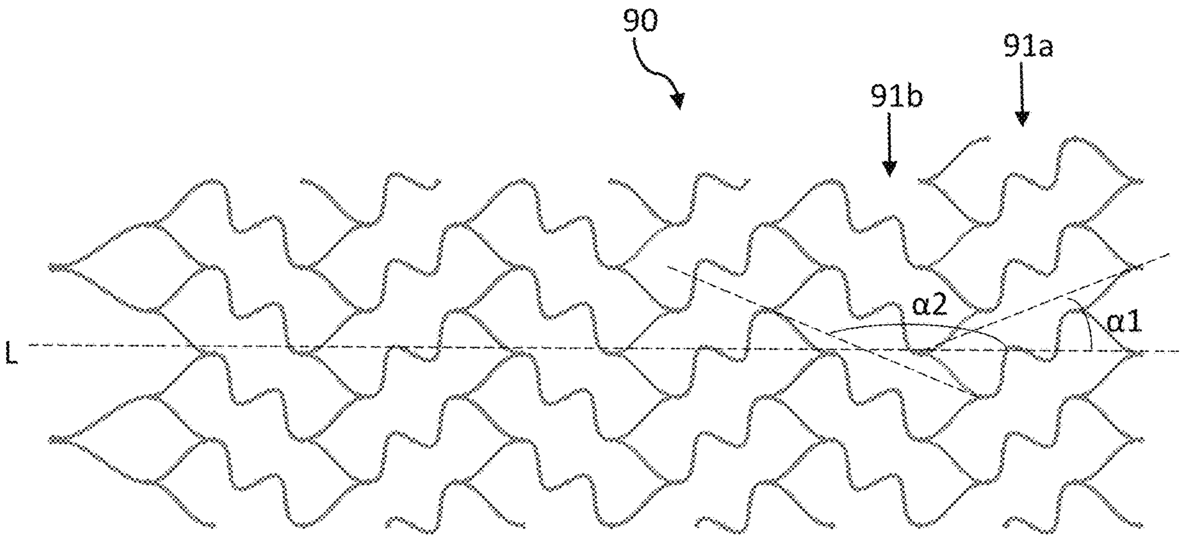
FIG. 9 is a perspective view of an exemplary device in a form of exemplary cell array in accordance with the present teachings.

According to some embodiments of the present teachings, the stent body could have all cells with the same configurations, such as shape, size, orientation, as well as the size of the struts, such as exemplary embodiment shown in FIGS. 4A, 4B, and 6. In another embodiment, the stent body could have some cells with various configuration from section to section. For example, as shown in FIG. 9, the first distal circumferential row (91*a*) of cells have a first cell axis forming a first angle ($\alpha$1) with the longitudinal axis "L" of the stent body, while the second circumferential row of cells (91*b*) proximal to the first row (91*a*) have a second cell axis forming a second angle ($\alpha$2) with the longitudinal axis "L" of the stent body. With this configuration, as the device (90) expands, it will rotate to a first direction at a first speed as the first row of cells (91*a*) expand, followed by a change of direction, rotate to a second direction at a second speed as the second row (91*b*) of cells expand.

Figure 10:
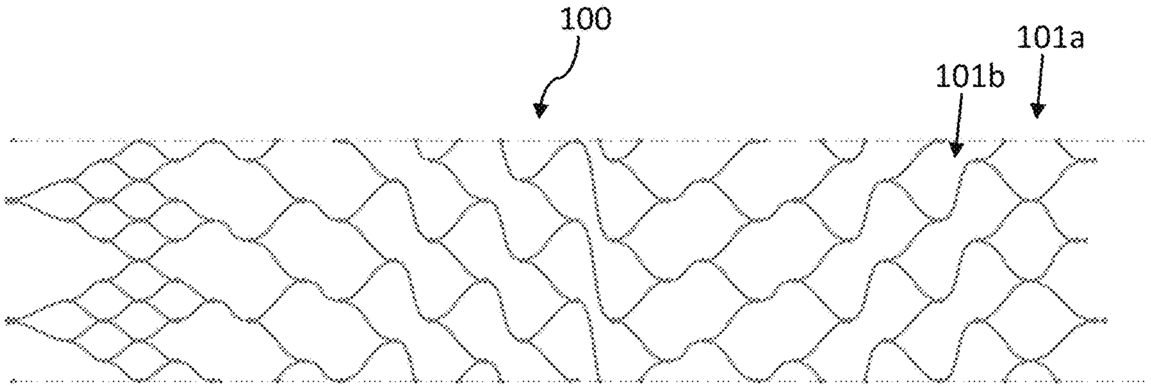
FIG. 10 is a perspective view of an exemplary device in a form of exemplary cell array in accordance with the present teachings.

In another embodiment, the stent body could have cells with different size and shape throughout out its entire length. For example, as shown in FIG. 10, the first distal circumferential row (101*a*) of cells have a first cell size and their cell axis are parallel to the longitudinal axis "L" of the stent body; the second circumferential row (101*b*) of cells proximal to the first row (101*a*) have a second cell size and angled cell axis to the longitudinal axis "L" of the stent body, several circumferential rows of cells proximal to the second circumferential row (101*b*) have a third cell size and a different angled cell axis to the longitudinal axis "L" of the stent body. Then followed by circumferential row of cells with reversed orientation and etc. With this configuration, as the device (100) expands, part of the stent body will expand without radial twisting, portions of the stent body will rotate initially with a first speed and torque strength toward a first direction as the second row (101*b*) of cells expand, followed by a change of axial rotation speed, torque strength as the rest circumferential rows of the cells expand.

Thus, according to some embodiments, the device deployment motion could be programed by changing in one or more of those above-mentioned design criteria, specifically, cell size, cell height to cell length ratio, the angle between cell axis to the longitudinal axis "L" of the device, cell strut size, cell strut curvature, and the number of cell in each circumference row and longitudinal row. According to some embodiments, a combinations of the angles between the cell axis and longitudinal axis "L" of the overall stent body, the height to length ratio of each cell, the cross section of struts forming each cell, the size of the cell, and the curvature profile of the cell struts can all be engineered in order to program the deployment movement of the device.

Thus, one skilled in the art should understand that the combinations of different factors of the cell and/or device design, could result various programmed deployment motion of the embolic capture device, such as clock wise rotation, counter-clockwise rotation, zig zag movement, accelerating motion along the length of the device and/or decelerating motion along the length of the device. Thus the present invention could be used to pre-program a stent body allowing its deployment motion to be customized according to the treatment location, the size of the blood clot to be captured, the patient anatomy, as well as the physician's preference and etc. Thus, the exemplary embodiment as shown in the figures, and description herein, should not be viewed as limiting to the scope of the present teaching.

According to some embodiments of the present teaching, the cell of the device could have a width of 1-10 mm, and a height of 1-5 mm. Each cell could be made of struts having 0.001-0.010" width and thickness. A device could have 2-10 row of cells, with 4-20 number of cells in each row. Upon deployment, the device could have 2 mm-8 mm in diameter, and 15 mm-60 mm in length. In yet another embodiment, the expansion ratio in diameter is 2-30. The angle between the cell axis and the longitudinal axis "L" of the device could ranges from 15-75 in either direction. The device could be designed to rotate in a continuous left-hand motion, a continuous counter clock wise motion, or a twisting motion such as a clock wise motion followed by a counter clock wise motion then followed by another clock wise motion and etc.

While most existing solutions in the market rely on the radial expansion of the device across the blood clot for capturing the clot, the torsion and torque provided in the present teaching creates a new force and motion that adds on to radial expansion of the device. As a result, the device not only engages the blood clot axially, but also engages the clot radially. This allows the device actively and securely engaging and retrieving the blood clot.

Figure 11A:
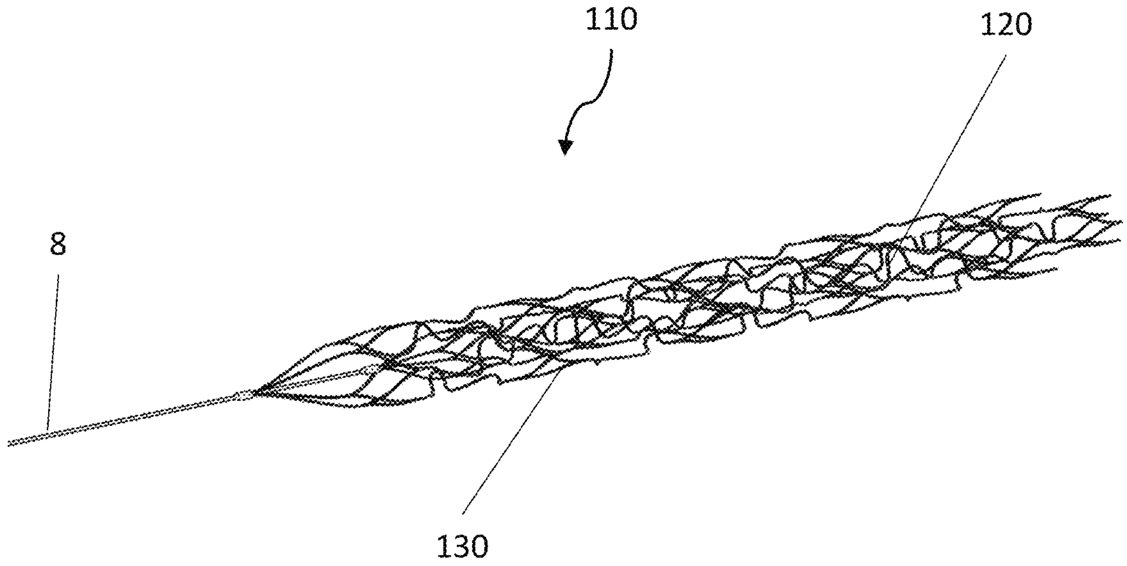
FIG. 11A is a perspective view of an exemplary device in a form of an outer exemplary cell array and an inner exemplary cell array in accordance with the present teachings.
Figure 11B:
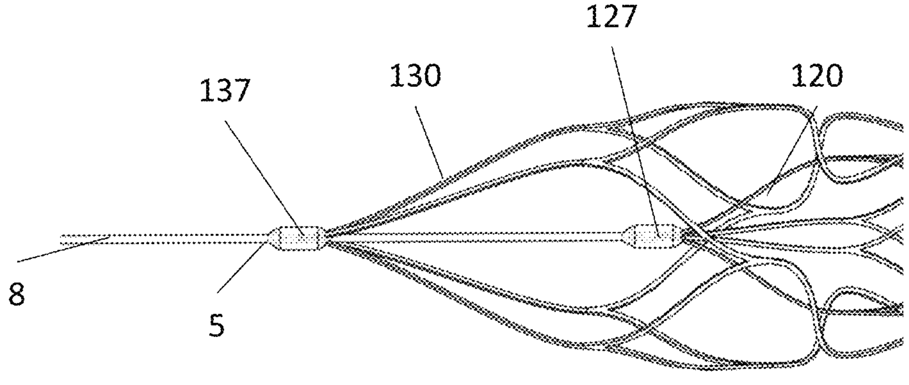
FIG. 11B is a perspective detailed view of an exemplary attachment between the proximal end of the exemplary device and a pusher shaft in accordance with the present teachings.
Figure 12A:
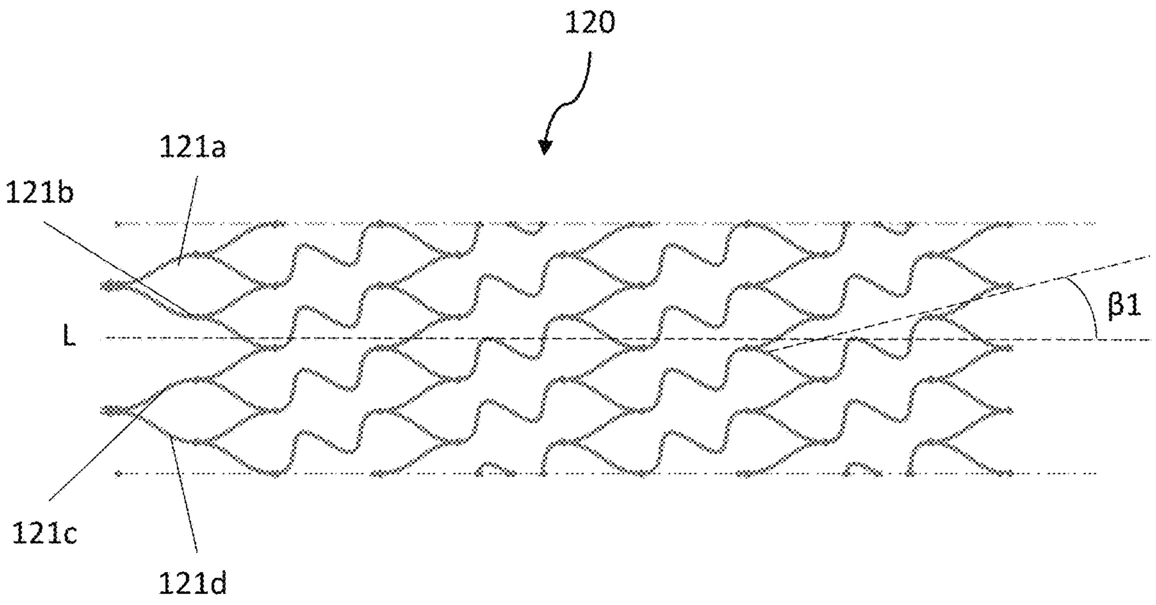
FIGS. 12A-12B are perspective views of an exemplary inner cell array in accordance with the present teachings.
Figure 12B:
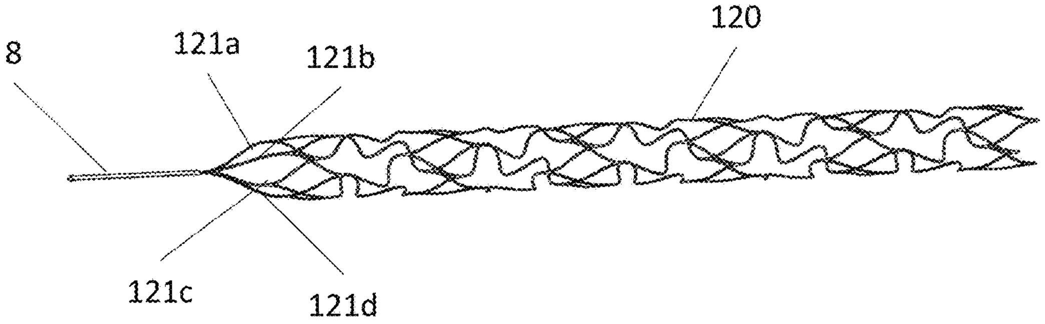
Figure 13A:
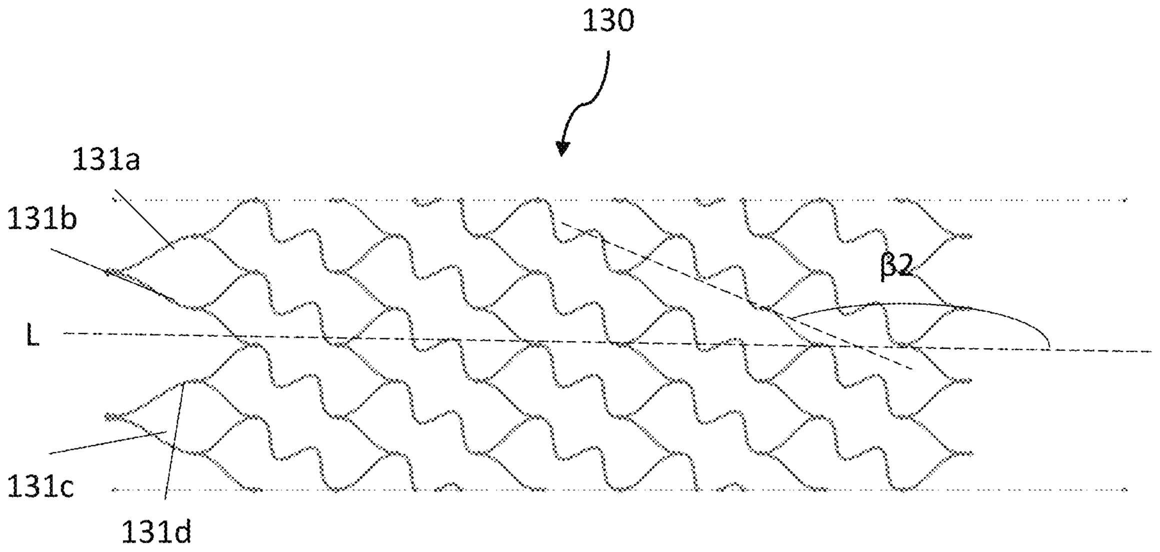
FIGS. 13A-13B are perspective views of an exemplary inner cell array in accordance with the present teachings.
Figure 13B:
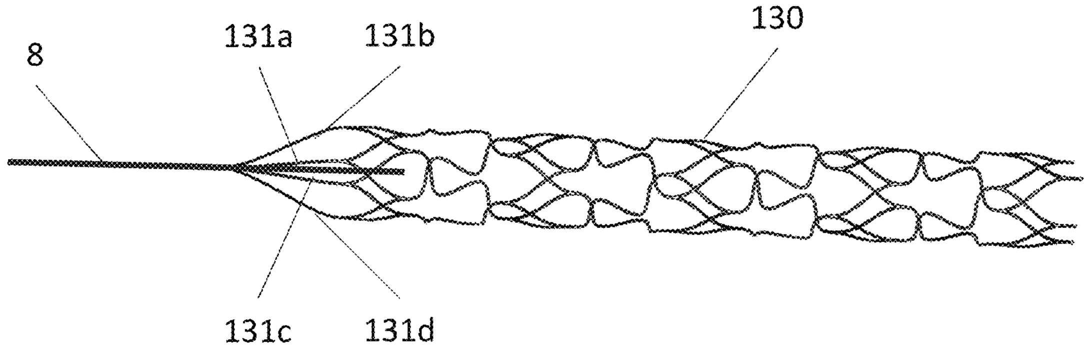

Now referring to FIGS. 11-13, an embolic capture device (110) has multiple layers of stent body. FIG. 11A illustrates multi-layer embolic capture device (110) in its deployed configuration with its proximal end joining a pusher shaft (8). FIG. 11B illustrates a detailed view of the connection between the embolic capture device (110) and pusher shaft (8) connection. FIG. 12A illustrates a hypothetical unwrapped view of the inner stent body (120) with its cell configuration. FIG. 12B illustrates an expanded profile of the inner stent body (120) alone. FIG. 13A illustrates a hypothetical unwrapped view of the outer stent body (130) with its cell configuration. FIG. 13B illustrates an expanded profile of the outer stent body (130) alone.

Now referring to FIG. 11B, similar to what has been described with reference to FIG. 2C, a marker band (127) in a shape of a tube is fixed over the proximal ends of connecting struts on the inner stent body (120) and the distal end of the pusher shaft (8). As seen in the figure, the proximal disc ends connecting struts extends beyond the proximal end of the marker band tube (127), the distal ball end of the pusher shaft (8) extends beyond the distal end of the marker band tube (127), and as marker band (127) fixed over the connecting struts of the inner stent body (120) and the pusher shaft, (8) a mechanical lock is formed between the pusher shaft (8) and the inner stent body (120).

Continue referring to FIG. 11B, the proximal connecting struts on the outer stent body (130) is also joined to a distal portion (5) of the pusher shaft (8), which is proximal to the marker band (127) that joins the connecting struts of the inner stent body (120) to the distal end of the pusher shaft (8). As shown in FIG. 11B, a marker band (137) in a shape of a tube is fixed over the proximal ends of connecting struts on the outer stent body (130) to the distal portion (5) of the pusher shaft (8). As seen in the figure, the marker band (137) slides over the pusher shaft and positioned at the distal portion (5) of the pusher shaft (8), the proximal disc ends connecting struts extends beyond the proximal end of the marker band tube (137). The marker band (137) fixed over the connecting struts of the outer stent body (130) and the pusher shaft, (8) forming a mechanical lock.

Now referring to FIG. 12A, the exemplary inner stent body (120) of the capture device (110) has a four rows of identical cells forming a complete circumference of the body with each row having four cells. As shown in the figure, all cells have the same size, and cross-section strut profile. Each cell formed by two struts with both distal and proximal end joins together. Each strut has a wavy curvature similar to what has been described in FIG. 8. Each cell has an axis forming a same angle "β1" with the longitudinal axis "L" of the inner stent body. Two cells next to each other from two adjacent rows, share a portion of the same strut. Two cells next to each other from the same row, also share a portion of the same strut. FIG. 12B illustrates the inner stent body in its deployed configuration, where the inner stent body assume a pre-set generally cylindrical body with a longitudinal lumen and a distal opening. According to one embodiment, the inner stent body layer also creates an instantaneous opening of blood flow. The proximal end of the inner stent body joins to struts which is configured to attach to a delivery system (not shown). In this exemplary inner stent body embodiment shown in FIGS. 12A-12B, as the inner stent body deploys, it will expand radially, axially rotate in a clock wise motion, in a sinusoidal fashion.

Although FIG. 12A illustrates inner stent body having identical cell size, one skilled in the art should understand that cell that made of the inner stent body could have various sizes, shapes, and orientations, similar to what has been disclosed above. For example, according to one embodiment of the present teaching, the distal portion of the inner stent body could have smaller cell size then the rest portion of the inner stent body. In another embodiment, the distal end of the inner stent body is configured to be closed in order to form a net for collecting distal embolus. Although FIG. 12A illustrates the inner stent body having 4 cells per row, one skilled in the art should understand the number of cells per row could range from 3-20, depending on the size of the cell, and treatment target.

Continue referring to FIG. 12A, four connecting struts (121_a_, 121_b_, 121_c_, & 121_d_) connects the proximal end of the proximal cells. The proximal ends of these four struts (121_a_, 121_b_, 121_c_, & 121_d_) then form a mechanical connection with the distal end of the pusher shaft (8) by a marker band (127) by means as described above. By the nature of the stent design, the connecting struts portion of the inner stent body can be flexible and yield easily compared to the stent body. Thus, these connecting struts (121_a_, 121_b_, 121_c_, & 121_d_) are configured to have a greater size, such as greater width and/or thickness, than the struts forming the cells on the inner stent body. According to one embodiment, the material mass at any axial location of the inner stent body across the entire circumference at any axial location of the inner stent body, including its connecting struts portion and stent body portion, are identical. Thus, the thickness and/or width of the struts could vary from the connecting struts portion of the inner stent body to the stent portion of the inner stent body in order to achieve this design goal. This would allow effective transfer of a physician proximal pushing strength to the entire inner stent body, and prevent kinking at the connecting portion of the inner stent body, and in turn lower the overall delivery force required.

According to one embodiment of the present teaching, the strut forming each cell has a width around 0.0025" and a thickness around 0.003". Upon deployment, each cell has a length of 10 mm and a height of 2.5 mm to 5 mm. The angle between cell axis and the longitudinal axis "L" of the device is around 30°. In one embodiment, the inner stent body has a diameter of the stent about 2 mm to 4 mm.

In one embodiment, the inner stent body is configured to rotate as the embolic capture device being deployed. In one embodiment, the speed, degree and direction of rotation of the inner stent body is programmed by the cell design. For example, the rotational rate of the inner stent body could be 90° to 720° upon complete deployment. In one embodiment, the outer stent body (130) could have a deployed diameter around 5 mm, and the inner stent body (120) could have a deployed diameter around 3 mm.

Now referring to FIG. 13A, the exemplary outer stent body (130) of the capture device (110) also has a four rows of identical cells forming a complete circumference of the body with each row having five cells. Similar to the exemplary inner stent body shown in FIGS. 12A-12B, as shown in the FIG. 13A, all cells have the same size, and cross-section strut profile. Each cell formed by two struts with both distal and proximal end joins together. Each strut has a wavy curvature similar to what has been described in FIG. 8. Each cell has an axis forming a same angle "β2" with the longitudinal axis "L" of the inner stent body. Two cells next to each other from two adjacent rows, share a portion of the same strut. Two cells next to each other from the same row, also share a portion of the same strut. FIG. 13B illustrates the outer stent body (130) in its deployed configuration, where the outer stent body (130) assume a pre-set generally cylindrical body with a longitudinal lumen and a distal opening. The proximal end of the outer stent body (130) joins to struts which is configured to attach to a pusher shaft. In this exemplary outer stent body embodiment shown in FIGS. 13A-13B, as the outer stent body (130) deploys, it will expand radially, axially rotate in a counter clock wise motion, in a sinusoidal fashion. That is as the device deploys, its inner stent body (120) and outer stent body (130) rotates in an opposite direction.

Although FIG. 13A illustrates outer stent body having identical cell size, one skilled in the art should understand that cell that made of the outer stent body could have various sizes, shapes, and orientations, similar to what has been disclosed above. For example, according to one embodiment of the present teaching, the portions of the outer stent body could have smaller cell size then the rest portion of the outer stent body. Although FIG. 13A illustrates the outer stent body having 4 cells per row, one skilled in the art should understand the number of cells per row could range from 3-20, depending on the size of the cell, and treatment target. In one embodiment, the number of rows as well as the number of cells per row on the outer stent body could be the same as the number of rows as well as the number of cells per row on the inner stent body. In another embodiment, the number of rows as well as the number of cells per row on the outer stent body could be different from the number of rows as well as the number of cells per row on the inner stent body.

Continue referring to FIG. 13A, four connecting struts (131*a*, 131*b*, 131*c*, & 131*d*) connects the proximal end of the proximal cell. The proximal ends of these four struts (131*a*, 131*b*, 131*c*, & 131*d*) then form a mechanical connection with a distal portion of the pusher shaft (no shown) by a marker band (not shown) by means as described above. Similar to what has been explained above, the thickness and/or width of the connecting struts (131*a*, 131*b*, 131*c*, & 131*d*) would vary from connecting struts portion to stent body portion in order to achieve an identical material mass across the entire circumference at any axial location of the outer stent body.

According to one embodiment, the distal end of the outer stent body attaches a radiopaque marker. For example, the distal end of the outer stent body could join to a marker band by crimp, weld, glue, and soldering or any other ways known in the field. In one embodiment, mark band connects to the distal end of the outer stent body in such way that it would not interfere the reentry of the device back inside the microcatheter.

According to one embodiment of the present teaching, the strut forming each cell has a width around 0.0025" and a thickness around 0.003". Upon deployment, each cell has a length of 10 mm and a height of 2.5 mm to 5 mm. The angle between cell axis and the longitudinal axis "L" of the device is around 30°. In one embodiment, the outer stent body has a diameter of the stent about 4 mm to 6 mm.

In one embodiment, the outer stent body is configured to rotate as the embolic capture device being deployed. In one embodiment, the speed, degree and direction of rotation of the outer stent body is programmed by the cell design. For example, the rotational rate of the inner stent body could be 90° to 720° upon complete deployment. In one embodiment, the outer stent body (130) could have a deployed diameter around 5 mm, and the inner stent body (120) could have a deployed diameter around 3 mm.

According to one embodiment of the present teaching, during embolic capture device deployment, the outer stent body rotates in an opposite direction to the inner stent body. According to one embodiment, as the device (110) deploys at the treatment site, the inner stent body (120) radially expands and axially rotates in a clock wise motion, the outer stent body (130) radially expands and axially rotates in a counter clock motion.

According to one embodiment of the present teaching, upon full deployment, the distal end of the inner stent body is configured to extend beyond the distal end of the outer stent body in both the delivery and deployment configuration of the embolic capture device. This is to prevent the inner stent body getting pinched into the outer stent body while being delivered and deployed. Thus, upon deployment, the distal end of the inner stent body (120) extends distally beyond the distal end of the outer stent body.

According to some embodiments of the present teaching, the embolic capture device housed inside a distal end portion of the microcatheter reaches the treatment site. As the clinician withdraw the microcatheter proximally, the embolic capture device is exposed, and expands as programmed. As both inner and outer stent body expand radially, they also rotates to an opposite direction. The combination of both rotation motion and expanding motion create a rotational force in engaging the clot. And the opposite rotation of the two stent body layer create a pinching force to the clot. This allows the embolic capture device securely captures in the blood clot.

Upon confirmation by the clinician, captured blood clot is then be retrieved back inside the microcatheter. To do so, a clinician pulls proximally on the pusher shaft. The four connecting struts (131*a*, 131*b*, 131*c*, & 131*d*) on the outer stent body (130) first collapse radially as it extends proximal into the microcatheter, followed by the collapsing of the outer stent body (130) and the four connecting struts (121*a*, 121*b*, 121*c*, & 121*d*) of the inner stent body, and lastly the rest of the device. As clinician continue pulls the pusher shaft (8) proximally, and the entire device collapses and enter back inside the microcatheter, the blood clot is being retrieved inside the microcatheter into a sheath. As the entire device (110) collapses and being retrieved inside the microcatheter. During retrieval process, according to one embodiment, the inner stent body (120) radially collapses and axially rotates in a counter clock wise motion, and the outer stent body (130) radially collapses and axially rotates in a clock wise motion. According to one embodiment, such multi-layer embolic capture device (110) design could improve clot engagement and retrieval.

According to one embodiment, in order to minimize the retrieval force, the proximal end portion of the embolic capture device with two layers of stent body is configured that the two layers of stent body as well as their connecting struts collapses sequentially so that the retrieval (resheathing) force of the inner stent body and outer sent body are stacked and not overlapped. This design is to lower the retrieval (resheathing) force compared to having the ramp start at the same location.

One skilled in the art should understand that FIGS. 11-13 illustrates only one exemplary embodiment of the multi-layer embolic capture device. According to above described, especially with reference to FIG. 3-10, variations to each design criteria could all be incorporated in order to program device deployment motion and achieve optimum clot capturing result. For example, by adjusting the inner and outer stent body's angles between each's cell axis and longitudinal axis "L", the device could be programmed to have a same or a different axial rotation direction, and/or a same or a different axial movement length i.e. rotational speed. In another example, by adjusting the cell size in the inner and outer stent body, the device could be programed to have a same or a different torque strength. In another example, one of the inner and/or outer stent body could be programed to deploy in a twist rotational motion, i.e. starting with a clock wise rotation, following by a counter clock wise rotation, then following by a lock wise rotation, and etc. According to one embodiment by program the inner and outer stent body of the device with different rotation configuration, the device could further engages and captures the clot successfully.

According to some embodiments of the present teaching, the inner stent body of the device could be of the same length as the outer stent body. In another embodiment, the inner stent body could be shorter than the outer stent body of the device such that the distal end of the inner stent body is proximal to the distal end of the outer stent body of the device. In an alternative embodiment, such as shown in FIG. 11, the inner stent body could be longer than the outer stent body of the device such that the distal end of the inner stent body extends beyond the distal end of the outer stent body. According to one embodiment of the present teaching, upon capturing blood clot, a clinician would withdraw the device back into a microcatheter. While the retrieving the device, both inner and outer stent bodies collapses radially as the device retracing back into a sheath. In one embodiment, the inner stent body and the outer stent body axially rotate at a different speed as the device retracing back into a sheath. In another embodiment, the inner stent body and the outer stent body axially rotate at a same speed as the device retracing back into a sheath.

According to some embodiment, the diameter ratio of the inner and outer stent body is 1:2 to 4:5. The expansion ratio of the outer stent body is the same as or greater than the expansion ratio of the inner stent body.

Figure 14:
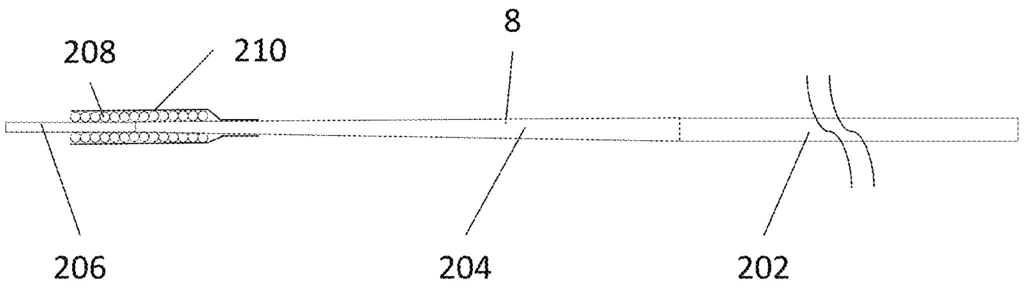
FIG. 14 is a perspective view of an exemplary pusher shaft in accordance with the present teachings.

Now referring to FIG. 14, the pusher shaft (8) has an elongated proximal portion (202) with a constant greater diameter, a gradually tapered intermediate portion (204), and an elongated distal portion (206) with a smaller diameter. According to one embodiment, such configuration would result the pusher shaft (8) having a relative flexible distal portion for going through the tortuous path of the neurovasculature without accidentally damaging the surrounding tissue, and a relative stiff proximal portion for providing pushability to the entire length of the pusher shaft.

According to one embodiment of the present teaching, the pusher shaft is made by a tapered nitinol rod with an *Af* transformation temperature less than 15° C. This is pre-programmed such that the nitinol rod is in its super elastic state at body temperature and at room temperature, so that the stiffness of the pusher shaft rod optimized for delivering the embolic capture device. According to one embodiment, the proximal portion (202) of the pusher shaft (8) has a dimeter of 0.015 to 0.020" and a length about 80 to 140 cm; the tapered intermediate portion (204) of the pusher shaft (8) has a length about 60 cm to 80 cm with its largest end matching the diameter of the proximal portion (202) and its smallest distal end matching the diameter of the distal portion (206) of the pusher shaft (8); and the distal portion (206) of the pusher shaft having an outer diameter of 0.005" to 0.010" and a length of about 5 cm to 30 cm.

Continue referring to FIG. 14, a coil layer (208) is fixed to the distal end portion (206) of the pusher shaft (8), extending from the distal end of the pusher shaft (8) proximally about 20 cm to 40 cm. With the coil layer (208), the distal end portion of the pusher shaft (8) is configured to maintain the flexibility of the nitinol rod while creating addition support in the pushability of the distal end portion of the pusher shaft (8). In addition, since the pusher shaft connecting to the stent body is pushing through the inside a microcatheter during delivery, the coil layer (208) is to reduce or fill the gap between the pusher shaft (8) and the microcatheter, which, as a consequence, increases the pushability as well as the torque support of the system during delivery. Because, with more gap between the microcatheter and the pusher shaft (8), the pusher shaft (8) could curve or form waves inside the microcatheter when being pushed by a physician, and the pushing force would be distracted and not be properly transformed. According to one embodiment, the coil layer (208) could be made of single or multifilar coil, with each filar size of 0.001" to 0.002" and a closed filar gap of less than 0.002". It could be made of stainless steel or other materials. Since the coil layer (208) is fixed to the distal end portion of the pusher shaft (8), the coil layer (208) is configured with an inner diameter of 0.005" to 0.010" matching the outer diameter of the distal end portion of the pusher shaft and an outer diameter of 0.012" to 0.015" matching the inner diameter of the microcatheter. In one embodiment, a distal portion of the coil layer (208) could be made of radiopaque material for visibility purpose. Such material could be platinum tungsten alloy, platinum iridium alloy, or platinum. In addition, a PTFE shrink tube (210) is used to cover the coil layer (208) in order to create a smooth outer surface and thereby reduce the friction between the pusher shaft assembly and the inside surface of the microcatheter.

According to some embodiments, the device is made of an elastic material, super-elastic material, or shape-memory alloy which allows said device to collapse into a generally straightened profile during the delivery process and resume and maintain its intended profile in vivo once it is deployed from the delivery catheter. In some embodiments, the device is made of stainless steel, nitinol, Titanium, Elgiloy, Vitalium, Mobilium, Ticonium, Platinore, Stellite, Tantalum, Platium, Hastelloy, CoCrNi alloys (e.g., trade name Phynox), MP35N, or CoCrMo alloys or other metallic alloys. Alternatively, in such embodiments, part or all of the device is made of any flexible, biocompatible material including, but not limited to polyester fabrics, Teflon-based materials, such as ePTFE, UHMPE, HDPE, polypropylene, polysulfone, polyurethanes, metallic materials, polyvinyl alcohol (PVA), extracellular matrix (ECM) isolated from a mammalian tissue, or other bioengineered materials, bioabsorbable polymers such as polylactic acid, polyglycolic acid, polycaprolactone, or other natural materials (e.g., collagen), or combinations of these materials that are well known to those skilled in the art.

In some embodiments of the present teachings, the device can be fabricated by laser-cutting or acid-etching a pattern into a preformed tube, then shape-setting to the intended deployed configuration. In such embodiment, the cell can be formed from a hollow tube that has been slotted using, for example, a machining laser or water drill or other method and then expanded to form the open structure. In another embodiment of the present teachings, the mesh can be formed from wire that is pre-bent into the desired shape and then bonded together to connect elements either by welding them or adhesively bonding them. They could be welded using a resistance welding technique or an arc welding technique, preferably while in an inert gas environment and with cooling control to control the grain structure in and around the weld site. These joints can be conditioned after the welding procedure to reduce grain size using coining or upset forging to optimize fatigue performance.

According to one embodiment of the present teachings, the device is fabricated from a tube and then shaped to its final configuration. In one embodiment, if a sufficiently elastic and resilient material such as nitinol, is used, the structure can be preformed into the finished shape and then elastically deformed and stowed during delivery so the shape will be elastically recovered after deployment.

One skilled in the art will recognize that the device described herein may be used in conjunction with infusing medication through the catheter directly into the thrombus site. Those embodiments with a distal net could limit the medicine, such as tPA (tissue plasminogen activator) that works to dissolve the clot, to be local and directly apply onto the blood clot. Specifically, the distal net of the device creates a closed volume which prevents the tPA from circulating through the system. Since this design also has a function of blocking the blood flow, it prevents blood from further bleeding, injection of medicine, and aspirating the blood out of tissues. For example, the pusher shaft could be configured to excrete tPA or any treatment medication. Those embodiments with a distal net, the space between the stent body and net, or two caps, is configured to create a closed contour which prevents the tPA from circulating systemically. In such event, after a certain amount of time, the emboli will be dissolved with the medicine, by aspiration, and/or retrieved by embolic capture device.

This exemplary embodiment provides an emboli engaging device that could perform thrombectomy without the help of a microcatheter. As such, using the embodiments of the present teachings can reduce vessel traumas, improve effectiveness in tortuosity, increase procedural success rate, and reduce the likelihood of losing the clot in tortuosity.

According to one embodiment of the present teachings, a radiopaque marker, coil or wire is winded to the elongated body to make the embolic capture device visible using radiographic imaging equipment such as X-ray, magnetic resonance, ultrasound or other imaging techniques. Markers as disclosed herein may be applied to the ends of any part of the devices, or even on the delivery system of the device. A radiopaque marker can be sewed, adhered, swaged riveted, otherwise placed and secured on the device, The radiopaque marker may be formed of tantalum, tungsten, platinum, iridium, gold, alloys of these materials or other materials that are known to those skilled in the art. The radiopaque marker can also be cobalt, fluorine or numerous other paramagnetic materials or other MR visible materials that are known to those skilled in the arts.

In addition, the delivery system could also be designed for aspiration purpose. For example, the pusher shaft is configured with an aspiration chamber. Such chamber is configured to open for aspiration. Upon delivery the distal end of the pusher shaft to the treatment location, the physician will be able to connect the aspiration pump, or a syringe, to the Pull Hypotube and suck in the clot. In some embodiments, the surface of the pusher shaft with the aspiration chamber is moderated to increase the aspiration effectiveness.

Various embodiments have been illustrated and described herein by way of examples, and one of ordinary skill in the art will appreciate that variations can be made without departing from the spirit and scope of the present teachings. The present teachings are capable of other embodiments or of being practiced or carried out in various other ways. Also, it is to be understood that the phraseology and terminology employed herein is for the purpose of description and should not be regarded as limiting.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

We claim:

1. A method for removing a blood clot comprising placing a guide wire across a blood clot, threading a microcatheter over the guide wire, wherein the microcatheter comprises a distal end, placing the distal end of the microcatheter distally to the blood clot, joining a pusher shaft to a proximal end of an embolic capture device, wherein the embolic capture device comprises a stent body, wherein the stent body comprises a plurality of circumferential rows of cells, advancing the pusher shaft distally so that the embolic capture device is placed at a location approximately to the blood clot, withdrawing the microcatheter proximally to engage the blood clot with the embolic capture device as the embolic capture device expands radially with at least two circumferential rows of cells of the embolic capture device rotating along its longitudinal axis of the stent body, wherein a first circumferential row of cells of the embolic capture device rotates with a first torque strength, and a second circumferential row of cells of the embolic capture device rotates with a second torque strength, wherein the first torque strength is different from the second torque strength; and pulling the pusher shaft to withdraw the embolic capture device and the blood clot proximally.

2. The method for removing a blood clot of claim 1, wherein the first circumferential row of cells of the embolic capture device rotates in a first direction, and the second circumferential row of cells of the embolic capture device rotates in a second direction, wherein the first direction is opposite to the second direction.

3. The method for removing a blood clot of claim 2, wherein at least one of the first and second circumferential rows of cells of the embolic capture device rotates in a clockwise rotation.

4. The method for removing a blood clot of claim 1, wherein the first circumferential row of cells of the embolic capture device rotates axially at a first speed, and the second circumferential row of cells of the embolic capture device rotates axially at a second speed, wherein the first rotation speed is different from the second rotation speed.

* * * * *